(12) United States Patent
Green et al.

(10) Patent No.: US 9,249,431 B2
(45) Date of Patent: Feb. 2, 2016

(54) PRODUCTION PROCESS

(75) Inventors: Edward Green, Marlow (GB); Matthew Crow, Witney (GB)

(73) Assignee: Green Biologics Limited, Abingdon, Oxfordshire (GB)

( * ) Notice: Subject to any disclaimer, the term of this patent is extended or adjusted under 35 U.S.C. 154(b) by 751 days.

(21) Appl. No.: 12/920,007

(22) PCT Filed: Feb. 27, 2009

(86) PCT No.: PCT/GB2009/000542
§ 371 (c)(1),
(2), (4) Date: Jan. 13, 2011

(87) PCT Pub. No.: WO2009/106835
PCT Pub. Date: Sep. 3, 2009

(65) Prior Publication Data
US 2011/0117615 A1    May 19, 2011

(30) Foreign Application Priority Data

Feb. 28, 2008  (GB) .................................. 0803762.4
Feb. 28, 2008  (GB) .................................. 0803764.0

(51) Int. Cl.
| C12P 7/16 | (2006.01) |
| C12P 7/42 | (2006.01) |
| C12P 7/52 | (2006.01) |
| C12N 1/20 | (2006.01) |
| C12P 7/04 | (2006.01) |
| C12P 7/40 | (2006.01) |

(52) U.S. Cl.
CPC ... *C12P 7/04* (2013.01); *C12N 1/20* (2013.01); *C12P 7/16* (2013.01); *C12P 7/40* (2013.01); *C12P 7/52* (2013.01); *Y02E 50/10* (2013.01)

(58) Field of Classification Search
None
See application file for complete search history.

(56) References Cited

U.S. PATENT DOCUMENTS

| | | |
|---|---|---|
| 1,315,585 A | 9/1919 | Weizmann |
| 4,424,275 A | 1/1984 | Levy |
| 4,443,542 A | 4/1984 | Hayashida et al. |
| 4,521,516 A | 6/1985 | Lemme et al. |
| 4,539,293 A | 9/1985 | Bergstrom et al. |
| 4,568,643 A | 2/1986 | Levy |
| 4,605,620 A | 8/1986 | Andersch et al. |
| 4,777,135 A | 10/1988 | Husted et al. |
| 4,882,277 A | 11/1989 | Czytko et al. |
| 5,063,156 A | 11/1991 | Glassner et al. |
| 5,132,217 A | 7/1992 | Gabelman |
| 5,182,199 A | 1/1993 | Hartley |
| 5,192,673 A | 3/1993 | Jain et al. |
| 5,210,032 A | 5/1993 | Kashket |
| 5,753,474 A | 5/1998 | Ramey |
| 5,755,967 A | 5/1998 | Meagher et al. |
| 6,358,717 B1 | 3/2002 | Blaschek et al. |
| 6,660,516 B1 | 12/2003 | Imamura et al. |
| 6,737,257 B2 | 5/2004 | Blum |
| 6,960,465 B1 | 11/2005 | Papoutsakis et al. |
| 7,256,016 B2 | 8/2007 | San et al. |
| 7,541,173 B2 | 6/2009 | Bramucci et al. |
| 2005/0089979 A1 | 4/2005 | Ezeji et al. |
| 2006/0011491 A1 | 1/2006 | Logan et al. |
| 2007/0031954 A1 | 2/2007 | Mairal et al. |
| 2007/0092957 A1 | 4/2007 | Donaldson et al. |
| 2007/0190605 A1 | 8/2007 | Bessler et al. |
| 2008/0293086 A1* | 11/2008 | Contag ........................... 435/29 |
| 2010/0062505 A1 | 3/2010 | Gunawardena et al. |

FOREIGN PATENT DOCUMENTS

| EP | 0125983 | 11/1984 |
| EP | 0338162 | 10/1989 |
| FR | 2583060 A1 | 12/1986 |
| GB | 1217035 | 12/1970 |
| GB | 2395481 A | 5/2004 |
| JP | 51026290 A | 3/1976 |
| JP | 62166882 A | 7/1987 |
| JP | 62289189 A | 12/1987 |
| JP | 2005-245439 A | 9/2005 |
| JP | 2005-261239 | 9/2005 |

(Continued)

OTHER PUBLICATIONS

Li et al., "An electrokinetic bioreactor: using direct electric current for enhanced lactic acid fermentation and product recovery," Tetrahedron, vol. 60, pp. 655-661 (2004); of record.*

(Continued)

*Primary Examiner* — Lora E Barnhart Driscoll
*Assistant Examiner* — Paul D. Pyla
(74) *Attorney, Agent, or Firm* — Knobbe, Martens, Olson & Bear, LLP

(57) ABSTRACT

The invention relates to a process for producing organic acids, acid derivatives thereof and/or organic alcohols. In particular, the invention relates to a process for culturing a butyric acid-producing micro-organism in a culture vessel; transferring a portion of the butyric acid which is produced in the culture vessel to a separate compartment; and then reintroducing a portion of the acids from the second compartment in a controlled manner into the culture vessel. The invention also relates to a process for making butanol. The invention further relates to a process for culturing a butyrate-producing microorganism in a first compartment of an electrochemical reactor, passing a direct current electric field across the electrochemical reactor and harvesting butyric acid or acid derivatives thereof in a second compartment of the reactor. The invention further relates to a process for producing butanol from the butyric acid.

16 Claims, 7 Drawing Sheets

(56) References Cited

FOREIGN PATENT DOCUMENTS

| WO | 9851813 | 11/1998 |
|---|---|---|
| WO | 02-29030 | 4/2002 |
| WO | 02086135 A2 | 10/2002 |
| WO | 2004046351 A1 | 6/2004 |
| WO | 2006-117536 | 11/2006 |
| WO | 2007-041269 | 4/2007 |
| WO | 2007-110606 | 4/2007 |
| WO | 2007041269 | 4/2007 |
| WO | 2007-110592 | 10/2007 |
| WO | 2008-052973 | 5/2008 |
| WO | 2008-072920 | 6/2008 |
| WO | 2008-072921 | 6/2008 |
| WO | 2008115080 A1 | 9/2008 |
| WO | 2008117068 A1 | 10/2008 |
| WO | 2008124490 A1 | 10/2008 |
| WO | 2008-137402 | 11/2008 |
| WO | 2010031793 | 3/2010 |

OTHER PUBLICATIONS

Peguin et al., "Enhanced Alcohol Yields in Batch Cultures of Clostridium Acetobutylicum Using a Three-Electrode Potentiometric System With Methyl Viologen As Electron Carrier," Biotechnology Letters, vol. 16, No. 3, pp. 269-274 (1994) (of record).*
Wu et al., Biotechnology and Bioengineering, vol. 82, No. 1, pp. 93-102; 2003; of record.*
Huang et al., Applied Biochemistry and Biotechnology, vol. 113-116, pp. 887-898; 2004; of record.*
Li, et al., An electrokinetic bioreactor: using direct electric current for enhanced lactic acid fermentation and product revovery, Tetrahedron (2004) -60 pp. 655-661.
Huang, C., et al., Application of electrodialysis to the production of organic acids: State-of-the-art and recent developments, Journal of Membrane Science (2007) 288, pp. h1-h12.
Mustacchi, et al., Enhanced Biotransformations and Product Recovery in a Membrane Bioreactor Through Application of a Direct Electric Current; Biotechnology & Bioengineering (2005) vol. 89, No. 1, pp. 18-23.
Lee, et al. Continuous Butanol Production Using Suspended and Immobilized Clostridium beijerinckii NCIMB 8052 with Supplementary Butyrate, Energy and Fuels, Nov. 2008, vol. 22, pp. 3459-3464.
Hayes, State of play in the biorefining industry, retrieved from www.carbolea.ul.ie/files/state_of_play.pdf, p. 90., the approximate date of publication was cited as 2007 in International Search Report for International Application No. PCT/GB2009/000542.
Barber, et al., Bacetriocin Production by Clostridium acetobutylicum in an Industrial Fermentation Process, Applied and Environmental Microbiology, Mar. 1979, vol. 37, No. 3, pp. 433-437.
Grupe, et al., Physiological Events in Clostridium acetobutylicum during the Shift from Acidogenesis to Solventogenesis in Continuous Culture and Presentation of a Model for Shift Induction, Applied and Environmental Microbiology, Dec. 1992, vol. 58, No. 12, pp. 3896-3902.
Zhao, et al., Expression of a Cloned Cyclopropane Fatty Acid Synthase Gene Reduces Solvent Formation in Clostridium acetobutylicum ATCC 824, Applied and Environmental Microbiology, May 2003, vol. 69, No. 5, pp. 2831-2841.
Zhao, et al., Intracellular Butyryl Phosphate and Acetyl Phosphate Concentrations in Clostridium acetobutylicum and Their Implications for Solvent Formation, Applied and Environmental Microbiology, Jan. 2005, vol. 71, No. 1, pp. 530-537.
Wu, et al., Extractive Fermentation for Butyric Acid Production From Glucose by Clostridium tyrobutyricum, Biotechnology and Bioengineering, Apr. 5, 2003, vol. 82, No. 1, pp. 93-102.
International Search Report and Written Opinion for International Application No. PCT/GB2009/000542, filed on Feb. 27, 2009, mailed on Oct. 15, 2010, 17 pages.

Atsumi, et al., "Non-fermentative pathways for synthesis of branched-chain higher alcohols as biofuels", Nature vol. 451, Jan. 3, 2008, pp. 86-90.
Huang, et al., "Continuous Production of Butanol by Clostridium acetobutylicum Immobilized in a Fibrous Bed Bioreactor", Applied Biochemistry and Biotechnology, vol. 115, 2004, pp. 887-898.
Moresi, et al., "Electrodialytic recovery of some fermentation products from model solutions: techno-economic feasibility study", Journal of Membrane Science, vol. 164, 2000, pp. 129-140.
Mustacchi, et al., "The Effect of Whole Cell Immobilisation on the Biotransformation of Benzonitrile and the Use of Direct Electric Current for Enhanced Product Removal", Biotechnology & Bioengineering, vol. 91, No. 4, Aug. 20, 2005, pp. 436-440.
Shin, et al., "Electronically enhanced ethanol fermentation by Clostridium thermocellum and *Saccharomyces Cerevisiae*" Appl Microbiol Biotechnol (2002) 58: 476-481.
Hwang, et al, "A Novel Three-compartmented Electrochemical Bioreactor for Enrichment of Strict Anaerobes Based on Metabolite Production" Biotechnology and Bioprocess Engineering, 2008, 13: 677-682.
Office Action issued on Jul. 31, 2008 for British Application No. GB0806093.1.
Office Action issued on Jul. 31, 2009 for British Application No. GB0905906.4.
Office Action issued on Aug. 23, 2010 for British Application No. GB0905906.4.
Office Action issued on Dec. 1, 2010 for British Application No. GB0905906.4.
Office Action issued on May 16, 2001 for British Application No. GB0905906.4.
Banat, et al., "Review: Ethanol production at elevated temperatures and alcohol concentrations: Part I: Yeasts in general" World Journal of Microbiology and Biotechnology, vol. 14, No. 6, Nov. 1998, pp. 809-821, XP-002531596.
Database EMBL [Online] Mar. 18, 1997, "T. thermosaccharolyticum BCS operon DNA" XP002531598 retrieved from EBI accession No. EMBL:Z92974 Database accession No. Z92974.
Inui, et al: "Expression of Clostridium acetobutylicum butanol synthetic genes in *Escherichia coli*" Applied Microbiology and Biotechnology, Springer Verlag, Berlin, DE, vol. 77, No. 6, Jan. 1, 2008, pp. 1305-1316.
Fong, et al: "Isolation and characterization of two novel ethanol-tolerant facultative-anaerobic thermophilic bacteria strains from waste compost" Extremophiles ; Life Under Extreme Conditions, Springer-Verlag, To, vol. 10, No. 5, Mar. 11, 2006, pp. 363-372.
Mendez, et al: "*Clostridium thermopapyrolyticum* New-Species A Cellulolytic Thermophile" International Journal of Systematic Bacteriology, vol. 41, No. 2, 1991, pp. 281-283.
Soh, et al: "*Clostridium thermopalmarium* New-Species A Moderately Thermophilic Butyrate-Producing Bacterium Isolated From Palm Wine In Senegal" Systematic and Applied Microbiology vol. 14, No. 2, Jan. 1, 1991, pp. 135-139.
Stroot, et al: "Description of a new butanol-producing thermophile Thermoanaerobacterium strain Me19" Abstracts of The General Meeting of The American Society for Microbiology, The Society, Washington, DC, US, vol. 99, Jan. 1, 1999, p. 510.
Woods, "The genetic engineering of microbial solvent production" Trends in Biotechnology, Elsevier Publications, Cambridge, GB, vol. 13, No. 7,Jul. 1, 1995, pp. 259-264.
Blaschek, et al. Bio-Butanol from Lignocellulose presentation (2008), pp. 1-11.
Cava, et al., Thermus thermophilus as biological model, Extremophiles (2009) 13: pp. 213-231.
Danner et al., "Bacillus stearothermophilus for Thermophilic Production of L-Latic Acid", Applied Biochemistry Biotechnology, vol. 70-72, pp. 895-903(1998).
Freier-Schroder, et al., "Butanol Formation by Clostridium Thermosaccharolyticum at Neutral PH", Biotechnology Letters (1998) vol. 11 No. 1, pp. 831-836.
Green, et al., "Genetic Manipulation of Acid and Solvent Formation in Clostridium acetobutylicum ATCC 824", Biotechnology & Bioengineering (1998) vol. 58, pp. 215-221.

(56) References Cited

OTHER PUBLICATIONS

Henne, et al., "The genome sequence of the extreme thermophile Thermus thermophilus", Nature Biotechnology vol. 22, No. 5 (2004) pp. 547-553.
Narumi, et al., "Construction of a New Shuttle Vector pSTE33 and its Stabilities in Bacillus Stearothermophilus, Bacillus Subtilis, and *Escherichia coli*", Biotechnology Letters, Aug. 1993, vol. 15, No. 8, pp. 815-820.
Nazina, et al., "Taxonomic study of aerobic thermophilic bacilli: descriptions of *Geobacillus subterraneus* gen. nov., sp. nov. and *Geobacillus uzenensis* sp. nov. from petroleum reservoirs and transfer of *Bacillus estearothermophilus, Bacillus thermocatenulatus, Bacillus thermoleovorans, Bacillus kaustophilus, Bacillus thermoglucosidasius* and *Bacillus thermodenitrificans* to *Geobacillus* as the new combinations *G. stearothermophilus, G. thermocatenulatus, G. thermoleovorans, G. kaustophilus, G. thermoglucosidasius and G. thermodenitrificans* Int'." Internat. Journ. System. Evolut. Microbiology, vol. 51 pp. 433-446 (2001).
Ohse, et al., "Application of Electroporation for Transformation in a Thermophilic Bacterium, Bacillus stearothermophilus", Memoirs of Fukui University of Technology, (1997) vol. 27, part 1, pp. 229-236.
Vollherbst-Schneck, et al., "Effect of Butanol on Lipid Composition and Fluidity of Clostridium acetobutylicum ATCC 824", Applied and Environmental Microbiology Jan. 1984, vol. 47, No. 1, pp. 193-194.
Wu, et al., "Protoplast Transformation of Bacillus stearothermophilus NUB36 by Plasmid DNA", Journal of General Microbiology, 1989, 135, pp. 1315-1324.
International Search Report and Written Opinion issued on Jun. 26, 2009 for International Application No. PCT/GB2009/000900.
United Kingdom Search Report issued on Sep. 7, 2009.
International Preliminary Report on Patentability issued on Oct. 5, 2010 for International Application No. PCT/GB2009/000900.
Narumi, et al., "A Newly Isolated Bacillus Stearothermophilus K1041 and Its Transformation by Electroporation", Biotechnology Techniques, vol. 6, No. 1, Oct. 8, 1992, pp. 83-86.
Branden, et al., "Prediction, Engineering and Design of Protein Structures," Garland Publising Inc., New York, p. 247, (1991).
Seffernick, et al., "Melamine Deaminase and Atrazine Chlorohydrolase: 98 Percent Identical but Functionally Difference," Journal of Bacteriology, Apr. 2001, vol. 183, No. 8, pp. 2405-2410.
Witokowski, et al., "Conversion of a B-Ketoacyl Synthase to a Malonyl Decarboxylase by Replacement of the Active-Site Cysteine with Glutamine," Biochemistry 1999, 38, pp. 11643-11650.
Sousa, et al., The ARO4 gene of Candida albicans encodes a tyrosine-sensitive DAHP synthase: evolution, functional conversation and phenotype of Aro3p-, Aro4p-deficient mutants, Microbiology (2002), 148, 1291-1303.
Zhou, et al., Global analysis of gene transcription regulation in prokaryotes, Cell. Mol. Life Sci. 63 (2006) pp. 2260-2290.
Kozak, "Initiation of translation in prokaryotes and eukaryotes," Elsevier, Gene, 234: 187-208, 1999.
Branch, Andrea D., "A good antisense molecule is hard to find", TIBS 23, Feb. 1998, pp. 45-50.
Nakagawa, et al. "AUH, a gene encoding an AU-specific RNA binding protein with intrinsic enoyl-CoA hydratase activity", Proc. Natl. Acad. Sci., USA, vol. 92, pp. 2051-2055, Mar. 1995.
Counago et al., "Gene replacement of adenylate kinase in the gram-positive thermophile Geobacillus stearothermophilus disrupts adenine nucleotide homeostasis and reduces cell viability", Extremophiles 9:135-144, 2005.
Thompson et al., "Heterologous expression of pyruvate decarboxylase in Geobacillus thermoglucosidasius", Biotechnology Letters 30:1359-1365, Mar. 27, 2008.
Holt, R. A., Production of Solvents by Clostridium acetobutylicum Cultures Maintained at Neutral pH, Applied and Environmental Microbiology (1984) 48:1166-1170.
Qureshi, N., Butanol Production from Corn Fiber Xylan Using Clostridium acetobutylicum, Biotechnology Progress (2006) 22:673-680.

\* cited by examiner

PRODUCTION PROCESS

This application is U.S. National Phase of International Application No. PCT/GB2009/000542, filed Feb. 27, 2009, designating the United States, and published as WO 2009/106835 on Sep. 3, 2009, which claims priority to British Patent Application Nos. 0803762.4 and 0803764.0, both of which filed Feb. 28, 2008.

The invention relates to a process for producing organic acids, acid derivatives thereof and/or organic alcohols. In particular, the invention relates to a process for culturing a butyric acid-producing micro-organism in a culture vessel; transferring a portion of the butyric acid which is produced in the culture vessel to a separate compartment; and then reintroducing a portion of the acids from the second compartment in a controlled manner into the culture vessel. The invention also relates to a process for making butanol. The invention also relates to a process for culturing a butyrate-producing micro-organism in a first compartment of an electrochemical reactor, passing a direct current electric field across the electrochemical reactor and harvesting butyric acid or acid derivatives thereof in a second compartment of the reactor. The invention further relates to a process for producing butanol from the butyric acid.

The fermentation of carbohydrates to organic solvents such as acetone, ethanol and butanol has been known for nearly 100 years. U.S. Pat. No. 1,315,585 (1919) describes such a process using bacterial "found in soil and cereals, e.g., maize, rice, flax, etc.". Such fermentation has traditionally been carried out using *Clostridium acetobutylicum*.

*Clostridium acetobutylicum* is a gram-positive, sporulating, obligate anaerobe capable of naturally producing acetone, butanol, and ethanol (ABE). *C. acetobutylicum* metabolism in early growth is geared toward accumulation of the acids acetate and butyrate. Once the cells reach stationary phase, these acids are converted to acetone and butanol, respectively. A smaller amount of ethanol also accumulates.

Up until the 1950s, commercial production of ABE was economically competitive with petrochemical production, but with the advent of low cost crude oil and alternative cheaper production methods for ABE, methods involving *Clostridium acetobutylicum* became less attractive.

With the current increased interest in non-petrochemical means of producing ABE and an increased global awareness of environmental issues, bacterial production of ABE has recently become more popular. Numerous different processes have or are being explored in order to increase yield of the ABE solvent. Many methods are aimed at the removal of the solvents (ABE) as the final products of fermentation. These include the removal of solvent by gas stripping (e.g. US 2005/0089979), by pervaporation using silicalite (e.g. U.S. Pat. No. 5,755,967) and by phase separation using fluorocarbons (e.g. U.S. Pat. No. 4,777,135). Two-stage fermentation methods, where one bacterial culture is used to produce organic acids that are then fed into a separate vessel where the acids are converted to solvents by a different strain of bacteria, are also known (U.S. Pat. No. 5,753,474). Co-cultures of *Clostridium* are also known, where one of the micro-organisms favours the production of butyric acid whilst the other converts the butyric acid to butanol (e.g. U.S. Pat. No. 4,539,293). Furthermore, genetically modified organisms such as genetically modified *E. coli* have been used to produce ABE (e.g. WO 2007/041269).

The present inventors have now found that increases in the yield of organic acids and organic alcohols in fermentation vessels can be obtained by removing organic acids from the culture medium and then reintroducing the removed acids in a controlled manner. Such acids may be used to control the pH of the fermentation media and also to control the growth and development of the micro-organisms in the media. The "recycling" of the acids also avoids the need to purchase other acids which might be needed for example to control pH.

The present inventors have also found that fermentation in a bioreactor through which a direct electric current is being passed increases production of organic acid and in particular ABE intermediates by appropriate micro-organisms. Such bioreactors have previously been described for use in the production of benzoic acid from benzonitrile by *Rhodococcus rhodococcus* (WO2004/046351) and for the production of lactic acid by *Lactobacillus* (Li et al., Tetrahedron 60 (2004), 655-661).

The micro-organisms involved in the current invention are those which are capable of producing the appropriate organic acid, in particular butyrate. Optionally, the micro-organisms also have a solventogenic growth phase, in which the organic acid is subsequently converted to the corresponding alcohol.

In these micro-organisms, the production of acid is an essential part of the growth cycle in order to produce energy for the cell. In organisms with a solventogenic growth phase, the production of acids is (at least in part) responsible for the switch to solventogenic growth where the acids are converted to alcohols. Although the acids are inhibitors of growth, they are required in order to facilitate the onset of solventogenesis.

In the process of the invention, acid or acid derivatives thereof are removed from the growth medium. This would be counterintuitive to the skilled person because it deprives the micro-organism of an energy source and, for micro-organisms with a solventogenic growth phase, it delays or prevents the onset of the solventogenesis growth phase, and hence it delays the production of the desired solvent.

The inventors have discovered, however, that the removal of acids from the growth medium has the adventitious effect of allowing cells to grow at their maximum rate in the absence of the acids. Optionally, on reaching the maximum cell density (at an earlier time than without acid removal) the acids which were previously removed are then added back to the culture vessel in a controlled manner (with or without additional carbon source) to induce the onset of solventogenesis and to allow their conversion to alcohol with a higher overall yield.

In a first embodiment, the invention provides a process for producing an acid of formula R—COOH, wherein R is an aliphatic $C_3$-$C_7$ alkyl or alkenyl group, or an acid derivative thereof, comprising: (i) culturing a micro-organism in a culture medium in a culture vessel, wherein the micro-organism is a R—COOH-producing micro-organism; (ii) transferring a first portion of acids of formula R—COOH or acid derivatives thereof which are produced in the culture vessel to a separate compartment; and (iii) introducing a second portion of the acids of formula R—COOH or acid derivatives obtained from the separate compartment into the culture vessel.

The invention also provides a process for producing butyric acid or an acid derivative thereof, comprising: (i) culturing a micro-organism in a culture medium in a culture vessel, wherein the micro-organism is a butyrate-producing micro-organism; (ii) transferring a first portion of butyric acid or acid derivatives thereof which are produced in the culture vessel to a separate compartment; and (iii) introducing a second portion of the butyric acid or acid derivatives obtained from the separate compartment into the culture vessel.

The invention further provides a process for producing an alcohol of formula R—CHOH, wherein R is an aliphatic $C_3$-$C_7$ alkyl or alkenyl group, comprising: (i) culturing a micro-organism in a culture medium in a culture vessel, wherein the micro-organism is one which is capable of producing R—COOH and R—CHOH; (ii) transferring a first portion of acids of formula R—COOH or acid derivatives thereof which are produced in the culture vessel to a separate compartment; (iii) introducing a second portion of the acids of formula R—COOH or acid derivatives obtained from the separate compartment into the culture vessel; and (iv) harvesting an alcohol of formula R—CHOH from the culture vessel.

The invention also provides a process for producing butanol, comprising: (i) culturing a micro-organism in a culture medium in a culture vessel, wherein the micro-organism is one which is capable of producing butyrate and butanol; (ii) transferring a first portion of butyric acid or acid derivatives thereof which are produced in the culture vessel to a separate compartment; (iii) introducing a second portion of the butyric acid or acid derivatives obtained from the separate compartment into the culture vessel; and (iv) harvesting butanol from the culture vessel.

A number of means for transferring the first portion of acid or acid derivatives thereof which are produced in the culture vessel to a separate compartment are known. Such means include using anion exchange resins and precipitation by positively charged polymers. The use of an electrochemical reactor is preferred. The separate compartment preferably contains a higher concentration of the acids or acid derivatives thereof compared to the concentration of the acids or acid derivatives thereof in the culture vessel.

The invention particularly relates to a process of the invention wherein the culture vessel is the first compartment of an electrochemical reactor, wherein step (ii) comprises applying a direct current electric field across the electrochemical reactor by means of an anode and cathode, wherein the electrodes which are used to apply the electric field are separated from the culture medium such that any micro-organisms in the culture medium do not come into contact with said electrodes, wherein the electrochemical reactor further comprises a second compartment which is placed between the first compartment and the anode and is separated from the first compartment by an anion-selective membrane, wherein anions in the first compartment are drawn through the anion-selective membrane by the electric field into the second compartment, from which they may be removed as acid or acid derivatives thereof; and wherein step (iii) comprises introducing a second portion of the acid or acid derivatives obtained from the second compartment into the culture vessel.

The invention further relates to a process of the invention wherein step (ii) comprises transferring at least a first portion of the culture medium from the culture vessel to the first compartment of an electrochemical reactor, applying a direct current electric field across the electrochemical reactor by means of an anode and cathode, wherein the electrochemical reactor further comprises a second compartment which is placed between the first compartment and the anode and is separated from the first compartment by an anion-selective membrane, wherein anions in the first compartment are drawn through the anion-selective membrane by the electric field into the second compartment, from which they may be removed as acid or acid derivatives thereof; and wherein step (iii) comprises introducing a second portion of the acid or acid derivatives obtained from the second compartment into the culture vessel.

In Step (iii), a portion of the acid or acid derivatives thereof obtained from the separate or second compartment is reintroduced into the culture vessel, preferably in a controlled manner.

Before the acid or acid derivatives are reintroduced into the culture vessel they may or may not be purified, fractionated or refined. Preferably, the acid or acid derivatives are used in the form in which they were present in the separate or second compartment. In other embodiments, the acid or acid derivatives are purified, fractionated or refined, for example to concentrate the acid or acid derivatives or to remove inhibitors of micro-organism growth.

The transfer of R—OOO$^-$ anions from the culture vessel to the separate or second compartment has a number of advantages:

(a) It removes feedback inhibition. In acid-producing micro-organisms, the acid generally acts as a feedback inhibitor of micro-organism growth. Hence the removal of at least some acid from the culture medium promotes the growth of the micro-organism. This means that the micro-organisms will grow at a faster than normal rate to reach a high cell density. Preferably, therefore, the acid is removed from the culture medium throughout, or substantially throughout, the exponential growth phase of the micro-organism.

(b) To provide a reservoir of acid as a potential product per se. Acids can be sold per se or can be converted into the corresponding alcohol by any suitable means.

(c) To provide a reservoir of acid which can be reintroduced into the culture vessel to control the pH of the culture medium. In particular, if acid is reintroduced at the point at which a solventogenic micro-organism's growth rate drops (i.e. at the transition phase), acid can be used to maintain the pH of the culture medium in order to counteract the increase in pH which is associated with solvent production.

Preferably, therefore, the portion of the acid or acid derivatives is reintroduced into the culture vessel at the late exponential phase (i.e. before the transition/stationary phase), during the transition phase or during the stationary, preferably early stationary, phase of the micro-organism's growth.

Preferably, the acid or acid derivatives are reintroduced into the culture vessel at a rate which maintains a constant or substantially constant pH in the culture vessel.

(d) To provide a reservoir of acid which can be reintroduced into the culture vessel to control the growth of the micro-organism in the culture vessel.

If acid is reintroduced during the exponential phase of a solventogenic micro-organism, it can be used to slow growth and induce the onset of the stationary phase and solventogenesis. This method means that growth is artificially halted by inhibition by acid. It is possible that if cells are allowed to go into transition or stationary phase the micro-organisms go beyond a "point of no return" and may sporulate. It may be beneficial to halt growth early to prevent micro-organisms going into a natural transition phase.

In particular, it is desirable to maximise growth rate in the absence of the acid or in the presence of a reduced concentration of acid. However, the culture will eventually move into stationary phase for different reasons (e.g. nutrient starvation, cofactor limitation).

Adding the acid back at a controlled rate means that the build-up of acid in the culture vessel never exceeds the inhibitory threshold of the micro-organism because the acid is converted to solvent.

Preferably, therefore, the acid or acid derivatives are reintroduced into the culture vessel during the exponential growth phase in order to slow the growth of the micro-organism and/or to induce the onset of the solventogenic phase of a biphasic micro-organism.

(e) To provide a reservoir of acid which can be reintroduced into the culture vessel to provide a substrate for solventogenic micro-organisms to convert to solvent.

In Step (iv), alcohol of formula R—CHOH (preferably butanol) is harvested from the culture vessel. This may be carried out by any suitable means. R—CHOH in the culture medium may be removed on a continuous or discontinuous basis. Examples of suitable means include gas-stripping, pervaporation, distillation and solvent extraction.

Additionally, other potential inhibitory products (e.g. acetate, lactate, formate, propionate, ascorbate and bicarbonate) may also be drawn into the second compartment and hence removed from the culture vessel. Whether or not these products are indeed inhibitory products will vary from micro-organism to micro-organism.

The invention also provides a process for producing an acid of formula R—COOH, wherein R is an aliphatic $C_3$-$C_7$ alkyl or alkenyl group, or an acid derivative thereof, comprising: (i) culturing a micro-organism in a culture medium in a culture vessel, wherein the micro-organism is a R—COOH-producing micro-organism, wherein the culture vessel is the first compartment of an electrochemical reactor, (ii) applying a direct current electric field across the electrochemical reactor by means of an anode and cathode, wherein the electrodes which are used to apply the electric field are separated from the culture medium such that micro-organisms in the culture medium do not come into contact with said electrodes, wherein the electrochemical reactor further comprises a second compartment which is placed between the first compartment and the anode and which is separated from the first compartment by an anion-selective membrane, and wherein R—OOO$^-$ anions in the first compartment are drawn through the anion-selective membrane by the electric field into the second compartment, from which they may be removed as R—COOH or acid derivatives thereof.

The invention also provides a process for producing butyric acid or acid derivatives thereof, comprising: (i) culturing a micro-organism in a culture medium in a culture vessel, wherein the micro-organism is a butyrate-producing micro-organism, and wherein the culture vessel is the first compartment of an electrochemical reactor, (ii) applying a direct current electric field across the electrochemical reactor by means of an anode and cathode, wherein the electrodes which are used to apply the electric field are separated from the culture medium such that micro-organisms in the culture medium do not come into contact with said electrodes, wherein the electrochemical reactor further comprises a second compartment which is placed between the first compartment and the anode and is separated from the first compartment by an anion-selective membrane, and wherein butyrate anions in the first compartment are drawn through the anion-selective membrane by the electric field into the second compartment, from which they may be removed as butyric acid or acid derivatives thereof.

The micro-organisms may either be cultured in the electrochemical reactor as discussed above or cultured elsewhere for example, at a remote location. In the latter case, culture medium, either with or without micro-organisms, may be transported to the electrochemical reactor in order to remove R—OOO$^-$ anions or butyrate anions.

In a further aspect, therefore, the invention provides process for producing an acid of formula R–COOH, wherein R is an aliphatic $C_3$-$C_7$ alkyl or alkenyl group, or an acid derivative thereof, comprising: (ia) culturing a micro-organism in a culture medium in a culture vessel, wherein the micro-organism is a R—COOH producing micro-organism, (ib) transferring at least a portion of the culture medium from the culture vessel to the first compartment of an electrochemical reactor, (ii) applying a direct current electric field across the electrochemical reactor by means of an anode and cathode, wherein the electrochemical reactor further comprises a second compartment which is placed between the first compartment and the anode and is separated from the first compartment by an anion-selective membrane, wherein R—OOO$^-$ anions in the first compartment are drawn through the anion-selective membrane by the electric field into the second compartment, from which they may be removed as R—COOH or acid derivatives thereof.

In a further aspect, therefore, the invention provides a process for producing butyric acid or acid derivatives thereof comprising: (ia) culturing a micro-organism in a culture medium in a culture vessel, wherein the micro-organism is a butyrate-producing micro-organism, (ib) transferring at least a portion of the culture medium from the culture vessel to the first compartment of an electrochemical reactor, (ii) applying a direct current electric field across the electrochemical reactor by means of an anode and cathode, wherein the electrochemical reactor further comprises a second compartment which is placed between the first compartment and the anode and is separated from the first compartment by an anion-selective membrane, wherein butyrate anions in the first compartment are drawn through the anion-selective membrane by the electric field into the second compartment, from which they may be removed as butyric acid or acid derivatives thereof.

In some embodiments of the invention, the portion of culture medium is passed through the first compartment of the electrochemical reactor more than once, e.g. 2, 3, or 4 times, in order to allow more acid to be removed to the second compartment.

Optionally, the process additionally comprises the step (iii) returning the (anion-depleted) portion of the culture medium to the culture vessel.

In some embodiments of the above invention where the culture vessel is remote from the electrochemical reactor, the micro-organisms are retained in the culture vessel, i.e. they are prevented by appropriate means from being transported to the electrochemical reactor. Examples of ways to retain the micro-organisms in the culture vessel include filters, sinters and cell recyclers.

In other embodiments of the invention, the culture medium which is transported to the electrochemical reactor includes micro-organisms which are being cultured in the culture vessel.

As used herein, the term "electrochemical reactor" refers to a vessel comprising a number of discrete compartments, across which it is possible to pass an electric field. The term "electrodes" refers to the anode and the cathode.

In embodiments of the invention where micro-organisms are transferred from a remote culture vessel to the electrochemical reactor with the culture medium or where the culture vessel is in the electrochemical reactor, the electrodes which are used to apply the electric field in the electrochemical reactor are preferably separated from the culture medium such that any micro-organisms in the culture medium do not come into contact with said electrodes. (Contact with electrodes is known to damage the cells of micro-organisms.)

Preferably, the separation of the electrodes from the culture medium is achieved by using a semi-permeable membrane or an ion-selective membrane. Examples of the latter membranes include membranes that selectively allow only anions to pass (i.e. anionic membranes), only cations to pass (i.e. cationic membranes) or neither anions or cations to pass (i.e. bipolar membranes). In such cases, certain ions and micro-organisms in the culture medium will be restricted to certain compartments.

Portions of the culture medium may be transferred from a remote culture vessel to the first compartment of the electrochemical reactor continuously or discontinuously. For example, portions of the culture medium may be pumped continuously to the first compartment of the electrochemical reactor or portions of the culture medium may be removed in batches from the culture vessel to the first compartment of the electrochemical reactor.

The transfer of portions of the culture medium to the electrochemical reactor may start when the micro-organisms are first cultured in the culture vessel. Generally, however, portions of the culture medium will start being transferred to the electrochemical reactor once the micro-organism is in its exponential phase and butyrate anions are being produced.

In the acid of formula R—COOH, R is an aliphatic $C_3$-$C_7$ alkyl group or an aliphatic $C_3$-$C_7$ alkenyl group. The acid may be branched or linear. Preferably, it is linear.

The acid may be saturated or unsaturated. Preferably it is saturated.

Examples of acids of formula R—COOH include methylpropanoic, n-butyric, pentanoic, hexanoic, heptanoic and octanoic acids. R is a preferably a $C_3$ alkyl group, most preferably $CH_3CH_2CH_2$—. Preferably, the acid of formula R—COOH is butyric acid.

As used herein, the term "acid of formula R—COOH or an acid derivative thereof" includes acids or acid derivatives of the acid, including metal and non-metal salts, esters and amides. Examples of metal salts include sodium, potassium and lithium salts. Examples of non-metal salts include ammonium salts. Preferably, the acids and acid derivatives thereof are subsequently converted to the corresponding alcohol of formula R—CHOH.

As used herein, the term "butyric acid or an acid derivative thereof" includes butyric acid or acid derivatives of butyric acid, including metal and non-metal salts, esters and amides. Examples of metal salts include sodium, potassium and lithium salts. Examples of non-metal salts include ammonium salts. Preferably, the acids and acid derivatives thereof are subsequently converted to butanol.

The micro-organism is one which is capable of producing R—COOH, preferably butyrate. Preferably, the organism is one which has the following genes, thus allowing the conversion of acetyl-CoA to butyryl-CoA: thiolase (acetyl-CoA acetyltransferase), 3-hydroxybutyryl-CoA dehydrogenase, crotonase and butyryl-CoA dehydrogenase.

Preferably, the micro-organism additionally comprises genes for the following, thus allowing conversion of butyryl-CoA to butyrate: phosphate butyltransferase (phosphotransbutyrylase) and butyrate kinase.

Examples of suitable micro-organisms which are capable of producing R—COOH, preferably butyrate, include bacteria and fungi, including *Clostridium, Acinetobacter, Arthrobacter, Bacillus, Bifidobacteria, Butyrivibrio, Escherichia, Enterococcus, Eubacterium Flavobacterium, Fusobacterium, Megasphaera, Nocardia, Pseudobutyrovibrio, Rhizobium, Rhodococcus, Roseburia, Streptomyces, Ralstonia, Taleabrevis, Ureibacillus, Thermoanaerobacter, Thermoanaerobacterium, Geobacillus, Pichia* and *Saccharomyces* species. In some embodiments of the invention, the micro-organism is not a *Lactobacillus*.

In other embodiments of the invention, the micro-organism may be a *Zymomonas, Pseudomonas, Alcaligenes, Klebsiella, Paenibacillus, Corynebacterium, Brevibacterium, Pichia, Candida,* or *Hansenula* species, preferably one which does or may be modified to produce butanol.

Particularly preferred micro-organisms include *Acinetobacter* sp., *Arthrobacter* sp. *Bacillus coagulans, Bacillus* sp., *Bacillus thermoglucosidasius* TN-T9, *Bifidobacterium adolescentis, Butyrivibrio fibrisolvens, Butyrivibrio hungatei, Butyrivibrio* spp., *Clostridium acetobutylicum, Clostridium acetobutylicum, Clostridium acetobutylicum* strain SA-1, *Clostridium aurantibutyricum, Clostridium beijerinckii, Clostridium beijerinckii, Clostridium butyricum, Clostridium celerecrescens, Clostridium kluyveri, Clostridium ljungdahlii, Clostridium pasteurianum, Clostridium proteoclasticum, Clostridium saccharobutylicum, Clostridium tetanomorphum, Clostridium thermobutyricum, Clostridium thermocellum, Clostridium therm osaccharolyticum, Clostridium tyrobutyricum, Eubacterium limosum, Eubacterium* spp., *F. nucleatum, Flavobacterium* sp., *Fusobacterium prauznitzii, Fusobacterium* spp., *Geobacillus thermoglucosidasius, Geobacillus toebii, Lactobacillus fermentum, Lactobacillus* spp., *Megasphaera elsdenii, Nocardia* sp., *Pseudobutyrovibrio ruminis, Pseudobutyrovibrio xylanivorans, Roseburia cecicola, Roseburia faecis, Roseburia hominis, Roseburia inulinivorans, Taleabrevis butyricans, Thermoanaerobacter ethanolicus,* and *Thermoanaerobacterium thermosaccharolyticum*.

In some embodiments, the micro-organism is preferably a bacterium, for example a gram-positive or gram-negative bacterium. In some embodiments, the micro-organism is a spore-forming bacterium. In other embodiments, the micro-organism is a saccharolytic bacterium.

The micro-organism may be an aerobic or an anaerobic micro-organism. Preferably it is an anaerobic micro-organism. Most preferably, it is an anaerobic bacterium. The bacteria may be a thermophilic bacterium.

In yet other embodiments, the micro-organism is a biphasic micro-organism.

As used herein, the term "biphasic" refers to a micro-organism which has an acidogenic growth phase and a solventogenic growth phase.

The term "acidogenic growth phase" refers to the ability of the micro-organism to convert a substrate into R—COOH, for example, into acetate and/or butyrate.

The term "solventogenic growth phase" refers to the ability of the micro-organism to convert the RCOOH into a solvent, preferably into one or more of acetone, ethanol and/or butanol.

In other embodiments, the micro-organism is a solvent-producing micro-organism.

As used herein, the term "solvent-producing" means that the micro-organism is one which is capable of producing a solvent, preferably a solvent such as acetone, ethanol, propanol and/or butanol. In certain particularly preferred embodiments, the micro-organism is a bacterium which is capable of producing ethanol, acetone and butanol.

In some preferred embodiments, the micro-organism is a micro-organism of the genus *Clostridium*. Preferred *Clostridium* species include *C. acetobutylicum, C. aurantibutyricum, C. beijerinckii, C. thermocellum, C. thermobutyricum, C. pasteurianum, C, kluyveri, C. saccharobutylicum, C. thermosaccharolyticum, C. saccharolyticum, C. tyrobutyricum* and *C. butyricum*, and butyrate-producing variants thereof.

In some preferred embodiments, the micro-organism is a micro-organism of the *Geobacillus, Thermoanaerobacterium, Thermoanaerobacter, Thermus* or *Ureibacillus*. Preferred species of other genera include *Geobacillus thermoglucosidasius, Geobacullis toebii, Thermoanaerobacter ethanolicus, Thermobacterium thermosaccharolyticum*.

In some embodiments of the invention, only one species of R—COOH-producing micro-organism will be present in the culture medium. In other embodiments, the culture medium will comprise 2, 3, 4, 5 or more different species of R—COOH-producing micro-organisms. The micro-organisms may be in non-immobilised or immobilised form. For example, the micro-organisms may be immobilised on a substrate or encapsulated. If they are encapsulated, they may be encapsulated within alginate beads or the like.

The culture medium is one which supports the growth of the micro-organism. It will include a carbon source which is capable of being converted by the micro-organism to R—COOH, preferably butyrate. Many such culture media are well known to those skilled in the art. In embodiments of the invention wherein the micro-organism is *Clostridium*, examples of suitable culture media include RCM (Reinforced Clostridial Medium, Oxoid) and industrial media containing molasses (such as that used by Barber et al. (1979) Applied and Environmental Microbiology 37:433-437; i.e. 134 parts molasses, 1 part calcium carbonate, 1 part starch, and 2 parts ammonium sulphate, by weight). Generally, the culture medium will be a liquid medium.

The carbon source is one which is capable of being converted by the micro-organism to an acid of formula R—COOH, preferably butyrate. In general, the carbon source is a carbohydrate monomer, dimer or chain, preferably of plant or animal origin.

Examples of suitable carbon sources include sugars such as glucose, sucrose, fructose, xylose, galactose, mannose, mannitol, molasses (e.g. from the sugar industry), glycerol (e.g. from biodiesel production), starches (e.g. from food waste or maize), black liquor (e.g. from the paper industry), hemicellulose, lignocellulose and cellulose (e.g. from plant material). Preferred carbon sources include glucose, sucrose, fructose, xylose, mannose, mannitol, glycerol, cellulose and xylan.

The culture medium buffer will be one which is appropriate for the chosen micro-organism(s). Appropriate buffers will be known to the persons skilled in the art.

In some embodiments of the invention, the buffer is an anionic buffer, for example a phosphate buffer ($PO_4^{2-}$) such as phosphate buffered saline, or a citrate-based buffer.

In other embodiments of the invention, the buffer is a cationic buffer, for example bis-Tris.

The use of a cationic buffer has a number of advantages. These include an increase in the efficiency of removal of butyrate, because such a buffer does not contain anions which compete with R—COO$^-$ anions for carrying the current. If appropriate ion-selective membranes are incorporated into the electrochemical reactor, loss of buffer can be prevented and hence pH can be controlled by adjusting the applied DC current; and the buffer can be retained within the first compartment of the electrochemical reactor. One disadvantage of cationic buffers, however, is their higher cost compared to anionic buffers.

The direct current electric field is applied across the electrochemical reactor by an anode and cathode, the latter electrodes being positioned such that the electric field is applied across all compartments of the electrochemical reactor.

The anode may be of any suitable metal. Preferably, the anode is platinised titanium, tantalum/iridium oxide coated titanium or platinum.

The cathode may be of any suitable metal. Preferred examples include stainless steel, titanium and platinised titanium.

The current density should be one that is appropriate to draw the anions which are produced from the first compartment into the second compartment. The current density is preferably at a level which does not produce any detrimental effect on the physiology of the micro-organism or on the stability of the culture medium.

Examples of suitable current densities include 10-30 mA/cm$^2$ direct current, preferably 15-25 mA/cm$^2$ and most preferably about 20 mA/cm$^2$.

The electric field is preferably applied constantly, i.e. all of the time, but in some embodiments of the invention, it is applied intermittently, e.g. there are periods of time when the electric field is applied and also periods of time when the electric field is not applied. Preferably, the field is applied for at least 50%, 75%, 90% or 95% of the time that the process is being carried out.

There may also be times when it is desirable to reverse the polarity of the current flow thought the electrochemical reactor, for example to remove build-up of products on the membranes.

The electrochemical reactor and/or culture vessel preferably comprises means for monitoring the pH level of the culture medium. Suitable means include pH probes and indicator solutions.

Preferably, the culture medium in the first compartment and/or in the culture vessel is stirred, by any suitable means. Examples include magnetic stirring, gas sparging and mechanical stirring.

The bioreactor and/or culture vessel preferably also comprises means to test for levels of various gases, such as $O_2$, $CO_2$, $H_2$ and $H_2S$.

The bioreactor and/or culture vessel also preferably comprises means for monitoring the temperature of the culture medium.

The first compartment of the electrochemical reactor is separated from the second compartment by an anion-selective membrane. Examples of such membranes include Tokuyama Soda Neosepta.

When the electric field is applied, the R—OOO$^-$ anions, preferably butyrate anions, which are produced by the micro-organisms are drawn (by virtue of their negative charge) from the first compartment through the anion-selective membrane to the second compartment where they accumulate.

In some embodiments of the invention, a cation-selective membrane is positioned between the second compartment of the electrochemical reactor and the anode. This prevents the movement of anions in the second compartment towards the anode.

Examples of cation-selective membranes include Nafion 450.

Other suppliers of ion-selective membranes are Fumatec and Eurodia.

In further embodiments of the invention, a bipolar membrane is positioned between the first compartment of the electrochemical reactor and the cathode. This prevents the passage of cations and anions from the first compartment towards the cathode. Furthermore, water hydrolysis within this bipolar membrane produces hydroxyl ions which may move into the first compartment thereby maintaining the pH in the first compartment by neutralizing the acid.

In other embodiments of the invention, a bipolar membrane is placed between the anode and the cathode immediately adjacent to the anode or immediately adjacent to the cathode or separate bipolar membranes are placed immediately adjacent to the anode and the cathode.

Examples of bipolar membranes include those by Tokuyama Co. Ltd. BP-1.

In other embodiments, a separation membrane (e.g. a microporous membrane or an ion exchange membrane) is used to separate the electrodes from the other compartments.

In some embodiments of the electrochemical reactor, an anolyte chamber is positioned between the anode and cathode, immediately adjacent to the anode.

In other embodiments of the electrochemical reactor, a catholyte chamber is positioned between the cathode and anode, immediately adjacent to the cathode.

The buffer in the anolyte and catholyte chambers provides electrical conductivity between the electrodes and the compartments of the electrochemical reactor. The buffers in the anolyte and catholyte chambers may be the same as that in the first compai tinent or may be different. Preferably, the buffer in the anolyte and catholyte chambers and the second compartment is the same, e.g. Tris Borate buffer (TBB).

Salt solutions can also be used in the anolyte and catholyte chambers. For example, sodium sulphate or acetate (100 mM) may be used.

The process of the invention may be operated in any suitable manner. For example, it may be operated as a batch process, fed-batch process or any form of continuous process.

In batch or fed-batch processes, R—COOH (preferably butyrate) may be harvested at any suitable time point after the start of the process, preferably at a time point when maximum yield of R—COOH (preferably butyrate) has been reached.

If portions of culture media are removed, it will generally be desirable to add new media to the culture vessel. Such media might have the same composition as the initial (starter) culture media, or it might have a different composition. For example, it might be supplemented with additional carbon sources, e.g. glucose, sucrose, fructose, xylose, mannose, mannitol, etc.

In another embodiment, the invention provides a process for producing an acid of formula R—COOH, wherein R is an aliphatic $C_3$-$C_7$ alkyl or alkenyl group, or an acid derivative thereof, comprising: (i) culturing a micro-organism in a culture medium in a culture vessel, wherein the micro-organism is a R—COOH-producing micro-organism, and wherein the culture, vessel is the first compartment of an electrochemical reactor, (ii) applying a direct current electric field across the electrochemical reactor by means of an anode and cathode, wherein the electrodes which are used to apply the electric field are separated from the culture medium such that any micro-organisms in the culture medium do not come into contact with said electrodes, wherein the electrochemical reactor further comprises a second compartment which is placed between the first compartment and the anode and is separated from the first compartment by an anion-selective membrane, wherein R—COO⁻ anions in the first compartment are drawn through the anion-selective membrane by the electric field into the second compartment, from which they may be removed as R—COOH or acid derivatives thereof; and (iii) reintroducing a portion of the R—COOH acid or acid derivatives thereof obtained from the second compartment into the culture vessel.

The invention also provides a process for producing an acid of formula R—COOH, wherein R is an aliphatic $C_3$-$C_7$ alkyl or alkenyl group, or an acid derivative thereof, comprising: (ia) culturing a micro-organism in a culture medium in a culture vessel, wherein the micro-organism is a R—COOH-producing micro-organism, (ib) transferring at least a portion of the culture medium from the culture vessel to the first compartment of an electrochemical reactor, (ii) applying a direct current electric field across the electrochemical reactor by means of an anode and cathode, wherein the electrochemical reactor further comprises a second compartment which is placed between the first compartment and the anode and is separated from the first compartment by an anion-selective membrane, and wherein R—COO⁻ anions in the first compartment are drawn through the anion-selective membrane by the electric field into the second compartment, from which they may be removed as R—COOH or acid derivatives thereof; and (iii) reintroducing a portion of the R—COOH acid or acid derivatives thereof obtained from the second compartment into the culture vessel.

In some embodiments of the invention, the acid or acid derivatives thereof are stored in a reservoir before a portion is reintroduced into the culture vessel.

Preferably, the acid of formula R—COOH is butyric acid.

In a further aspect, the micro-organism is one which is also capable of producing R—CHOH and the process additionally comprises the step (iv) harvesting an alcohol of formula R—CHOH from the culture vessel.

In particular, the invention provides a process for producing an alcohol of formula R—CHOH, wherein R is an aliphatic $C_3$-$C_7$ alkyl or alkenyl group or an acid derivative thereof, comprising: (i) culturing a micro-organism in a culture medium in a culture vessel, wherein the micro-organism is one which is capable of producing R—COOH and R—CHOH, and wherein the culture vessel is a first compartment of an electrochemical reactor, (ii) applying a direct current electric field across the electrochemical reactor by means of an anode and cathode, wherein the electrodes which are used to apply the electric field are separated from the culture medium such that any micro-organisms in the culture medium do not come into contact with said electrodes, wherein the electrochemical reactor further comprises a second compartment which is placed between the first compartment and the anode and is separated from the first compartment by an anion-selective membrane, and wherein RCOO⁻ anions in the first compartment are drawn through the anion-selective membrane by the electric field into the second compartment, from which they may be removed as R—COOH acid or acid derivatives thereof; (iii) reintroducing a portion of the acid of formula R—COOH or acid derivatives thereof obtained from the second compartment into the culture vessel; and (iv) harvesting an alcohol of formula R—CHOH from the culture vessel.

A further aspect of the invention provides a process for producing an alcohol of formula R—CHOH, wherein R is an aliphatic $C_3$-$C_7$ alkyl or alkenyl group, or an acid derivative thereof, comprising: (ia) culturing a micro-organism in a culture medium in a culture vessel, wherein the micro-organism is one which is capable of producing R—COOH and R—CHOH, (ib) transferring at least a portion of the culture medium from the culture vessel to the first compartment of an electrochemical reactor, (ii) applying a direct current electric field across the electrochemical reactor by means of an anode and cathode, wherein the electrochemical reactor further comprises a second compartment which is placed between the first compartment and the anode and is separated from the first compartment by an anion-selective membrane, and wherein RCOO⁻ anions in the first compartment are drawn through the anion-selective membrane by the electric field into the second compartment, from which they may be removed as R—COOH or acid derivatives thereof; and (iii) reintroducing a portion of the R—COOH acid or acid derivatives thereof obtained from the second compartment into the culture vessel; and (iv) harvesting an alcohol of formula R—CHOH from the culture vessel.

In the above processes, R is a preferably a C3 alkyl group, most preferably $CH_3CH_2CH_2$—.

In Step (iii), a portion of the acid or acid derivatives thereof obtained from the second compartment is reintroduced into the culture vessel, preferably in a controlled manner.

Before the acid or acid derivatives are reintroduced into the culture vessel they may or may not be purified or refined. Preferably, the acid or acid derivatives are used in the form in which they were present in the second compartment. In other embodiments, the acid or acid derivatives are purified or refined, for example to concentrate the acid or acid derivatives or to remove inhibitors of micro-organism growth.

The transfer of R—COO⁻ anions from the first comparwent to the second compartment has a number of advantages:

(a) It removes feedback inhibition. In acid-producing micro-organisms, the acid generally acts as a feedback inhibitor of micro-organism growth. Hence the removal of at least some acid from the culture medium promotes the growth of the micro-organism. This means that the micro-organisms will grow at a faster than normal rate to reach a high cell density.

Preferably, therefore, the acid is removed from the culture medium throughout, or substantially throughout, the exponential growth phase of the micro-organism.

(b) To provide a reservoir of acid as a potential product per se. Acids can be sold per se or can be converted into the corresponding alcohol by any suitable means.

(c) To provide a reservoir of acid which can be reintroduced into the culture vessel to control the pH of the culture medium. In particular, if acid is reintroduced at the point at which a solventogenic micro-organism's growth rate drops (i.e. at the transition phase), acid can be used to maintain the pH of the culture medium in order to counteract the increase in pH which is associated with solvent production.

Preferably, therefore, the portion of the acid or acid derivatives is reintroduced into the culture vessel at the late exponential phase (i.e. before the transition/stationary phase), during the transition phase or during the stationary, preferably early stationary, phase of the micro-organism's growth.

Preferably, the acid or acid derivatives are reintroduced into the culture vessel at a rate which maintains a constant or substantially constant pH in the culture vessel.

(d) To provide a reservoir of acid which can be reintroduced into the culture vessel to control the growth of the micro-organism in the culture vessel.

If acid is reintroduced during the exponential phase of a solventogenic micro-organism, it can be used to slow growth and induce the onset of the stationary phase and solventogenesis. This method means that growth is artificially halted by inhibition by acid. It is possible that if cells are allowed to go into transition or stationary phase the micro-organisms go beyond a "point of no return" and may sporulate. It may be beneficial to halt growth early to prevent micro-organisms going into a natural transition phase.

In particular, it is desirable to maximise growth rate in the absence of the acid or in the presence of a reduced concentration of acid. However, the culture will eventually move into stationary phase for different reasons (e.g, nutrient starvation, cofactor limitation). Adding the acid back at a controlled rate means that the build-up of acid in the culture vessel never exceeds the inhibitory threshold of the micro-organism because the acid is converted to solvent.

Preferably, therefore, the acid or acid derivatives are reintroduced into the culture vessel during the exponential growth phase in order to slow the growth of the micro-organism and/or to induce the onset of the solventogenic phase of a biphasic micro-organism.

(e) To provide a reservoir of acid which can be reintroduced into the culture vessel to provide a substrate for solventogenic micro-organisms to convert to solvent.

In Step (iv), alcohol of formula R—CHOH is harvested from the culture vessel. This may be carried out by any suitable means. R—CHOH in the culture medium may be removed on a continuous or discontinuous basis. Examples of suitable means include gas-stripping, pervaporation, distillation and solvent extraction.

Additionally, other potential inhibitory products (e.g. acetate, lactate, formate, propionate, ascorbate and bicarbonate) may also be drawn into the second compartment and hence removed from the culture vessel. Whether or not these products are indeed inhibitory products will vary from micro-organism to micro-organism.

In another embodiment, the invention provides a process for producing butyric acid or acid derivatives thereof, comprising: (i) culturing a micro-organism in a culture medium in a culture vessel, wherein the micro-organism is a butyrate-producing micro-organism, and wherein the culture vessel is the first compartment of an electrochemical reactor, (ii) applying a direct current electric field across the electrochemical reactor by means of an anode and cathode, wherein the electrodes which are used to apply the electric field are separated from the culture medium such that any micro-organisms in the culture medium do not come into contact with said electrodes, wherein the electrochemical reactor further comprises a second compartment which is placed between the first compartment and the anode and is separated from the first compartment by an anion-selective membrane, wherein butyrate anions in the first compartment are drawn through the anion-selective membrane by the electric field into the second compartment, from which they may be removed as butyric acid or acid derivatives thereof; and (iii) reintroducing a portion of the butyric acid or acid derivatives thereof obtained from the second compartment into the culture vessel.

The invention also provides a process for producing butyric acid or acid derivatives thereof comprising: (ia) culturing a micro-organism in a culture medium in a culture vessel, wherein the micro-organism is a butyrate-producing micro-organism, (ib) transferring at least a portion of the culture medium from the culture vessel to the first compartment of an electrochemical reactor, (ii) applying a direct current electric field across the electrochemical reactor by means of an anode and cathode, wherein the electrochemical reactor further comprises a second compartment which is placed between the first compartment and the anode and is separated from the first compartment by an anion-selective membrane, and wherein butyrate anions in the first compartment are drawn through the anion-selective membrane by the electric field into the second compartment, from which they may be removed as butyric acid or acid derivatives thereof; and (iii) reintroducing a portion of the butyric acid or acid derivatives thereof obtained from the second compartment into the culture vessel.

In some embodiments of the invention, the butyric acid or acid derivatives thereof are stored in a reservoir before a portion is reintroduced into the culture vessel.

In a further aspect, the micro-organism is one which is also capable of producing butanol and the process additionally comprises the step (iv) harvesting butanol from the culture vessel.

In particular, the invention provides a method of producing butanol, comprising: (i) culturing a micro-organism in a culture medium in a culture vessel, wherein the micro-organism is capable of producing butyrate and butanol, and wherein the culture vessel is a first compartment of an electrochemical reactor, (ii) applying a direct current electric field across the electrochemical reactor by means of an anode and cathode, wherein the electrodes which are used to apply the electric field are separated from the culture medium such that any micro-organisms in the culture medium do not come into contact with said electrodes, wherein the electrochemical reactor further comprises a second compartment which is placed between the first compartment and the anode and is separated from the first compartment by an anion-selective membrane, and wherein butyrate anions in the first compartment are drawn through the anion-selective membrane by the electric field into the second compartment, from which they may be removed as butyric acid or acid derivatives thereof; (iii) reintroducing a portion of the butyric acid or acid derivatives thereof obtained from the second compartment into the culture vessel; and (iv) harvesting butanol from the culture vessel.

A further aspect of the invention provides a process for producing butanol comprising: (ia) culturing a micro-organism in a culture medium in a culture vessel, wherein the micro-organism is capable of producing butyrate and butanol, (ib) transferring at least a portion of the culture medium from the culture vessel to the first compartment of an electrochemical reactor, (ii) applying a direct current electric field across the electrochemical reactor by means of an anode and cathode, wherein the electrochemical reactor further comprises a second compartment which is placed between the first compartment and the anode and is separated from the first compartment by an anion-selective membrane, and wherein butyrate anions in the first compartment are drawn through the anion-selective membrane by the electric field into the second compartment, from which they may be removed as butyric acid or acid derivatives thereof; (iii) reintroducing a portion of the butyric acid or acid derivatives thereof obtained from the second compartment into the culture vessel; and (iv) harvesting butanol from the culture vessel.

In Step (iii), a portion of the butyric acid or acid derivatives thereof obtained from the second compartment is reintroduced into the culture vessel, preferably in a controlled manner.

The transfer of butyrate from the first compartment to the second compartment has a number of advantages:

(a) It removes feedback inhibition. In butyrate-producing micro-organisms, butyrate generally acts as a feedback inhibitor of micro-organism growth. Hence the removal of at least some butyrate from the culture medium promotes the growth of the micro-organism. This means that the micro-organisms will grow at a faster than normal rate to reach a high cell density.

(b) To provide a reservoir of butyrate as a potential product per se. Butyrate can be sold per se or can be converted into butanol by any suitable means.

(c) To provide a reservoir of butyrate which can be reintroduced into the culture vessel to control the pH of the culture medium. In particular, if butyrate is reintroduced at the point at which a solventogenic micro-organism's growth rate drops (i.e. at the transition phase), butyrate can be used to maintain the pH of the culture medium in order to counteract the increase in pH which is associated with solvent production.

(d) To provide a reservoir of butyrate which can be reintroduced into the culture vessel to control the growth of the micro-organism in the culture vessel.

If butyrate is reintroduced during the exponential phase of a solventogenic micro-organism, it can be used to slow growth and induce the onset of the stationary phase and solventogenesis. This method means that growth is artificially halted by inhibition by butyrate. It is possible that if cells are allowed to go into transition or stationary phase the micro-organisms go beyond a "point of no return" and may sporulate. It may be beneficial to halt growth early to prevent micro-organisms going into a natural transition phase.

In particular, it is desirable to maximise growth rate in the absence of the butyrate or in the presence of a reduced concentration of butyrate. However, the culture will eventually move into stationary phase for different reasons (e.g. nutrient starvation, cofactor limitation).

Adding the butyrate back at a controlled rate means that the build-up of butyrate in the culture vessel never exceeds the inhibitory threshold of the micro-organism because the butyrate is converted to solvent.

(e) To provide a reservoir of butyrate which can be reintroduced into the culture vessel to provide a substrate for solventogenic micro-organisms to convert to solvent.

In Step (iv), butanol is harvested from the culture vessel. This may be carried out by any suitable means. Butanol in the culture medium may be removed on a continuous or discontinuous basis, Examples of suitable means include gas-stripping, pervaporation, distillation and solvent extraction.

Additionally, other potential inhibitory products (e.g. acetate, lactate, formate, propionate, ascorbate and bicarbonate) may also be drawn into the second compartment and hence removed from the culture vessel. Whether or not these products are indeed inhibitory products will vary from micro-organism to micro-organism.

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

EXAMPLES

Example 1

Effect of Removing Acid From A Fermentation of ABE Clostridia

A 0.5 ml stock of spores of *C. acetobutylicum* strain ATCC 824 (obtained from a commercial supplier and obtainable from the ATCC) was activated by heating at 80° C. for 10 minutes, then cooled on ice for 5 minutes. Activated spores were then aseptically transferred to a serum bottle containing 30 ml of sterile RCM (Reinforced Clostridial Medium, Oxoid) and incubated overnight at 37° C.

100 ml of RCM in a serum bottle was then inoculated with 1ml of the overnight culture and incubated at 37° C. until the culture turned cloudy and bubbles appeared on the surface of the culture medium. A 2 L fermentation vessel containing 2 L of 2×CGM ('Clostridial Growth medium', preheated to 37° C., stirred at 150 rpm and maintained at pH 6.6) was then inoculated with 40 ml of the overnight culture.

Samples were taken periodically over the course of the experiment and the optical density was measured (attenuance of light at 600 nm).

The fermentation procedure was repeated a second time, but an electrokinetic bioreactor (the 'stack', Eurodia, France) was connected to the fermentation vessel on a loop via a pump. The pump was switched on after the onset of growth to pump the fermentation medium through the stack. A potential difference that generated a current equivalent to 20 mA/cm$^2$ (of anion exchange membrane) was applied to the 'stack' to allow passage of negatively charged species (e.g. butyrate, acetate) across the positively charged anion exchange membrane from the fermentation medium to the collection channel, where the acid can be removed and stored. The collection channels contained 100 mM $Na_2SO_4$.

Again, samples were taken periodically over the course of the experiment and the optical density was measured (attenuance of light at 600 nm).

Figure 1:
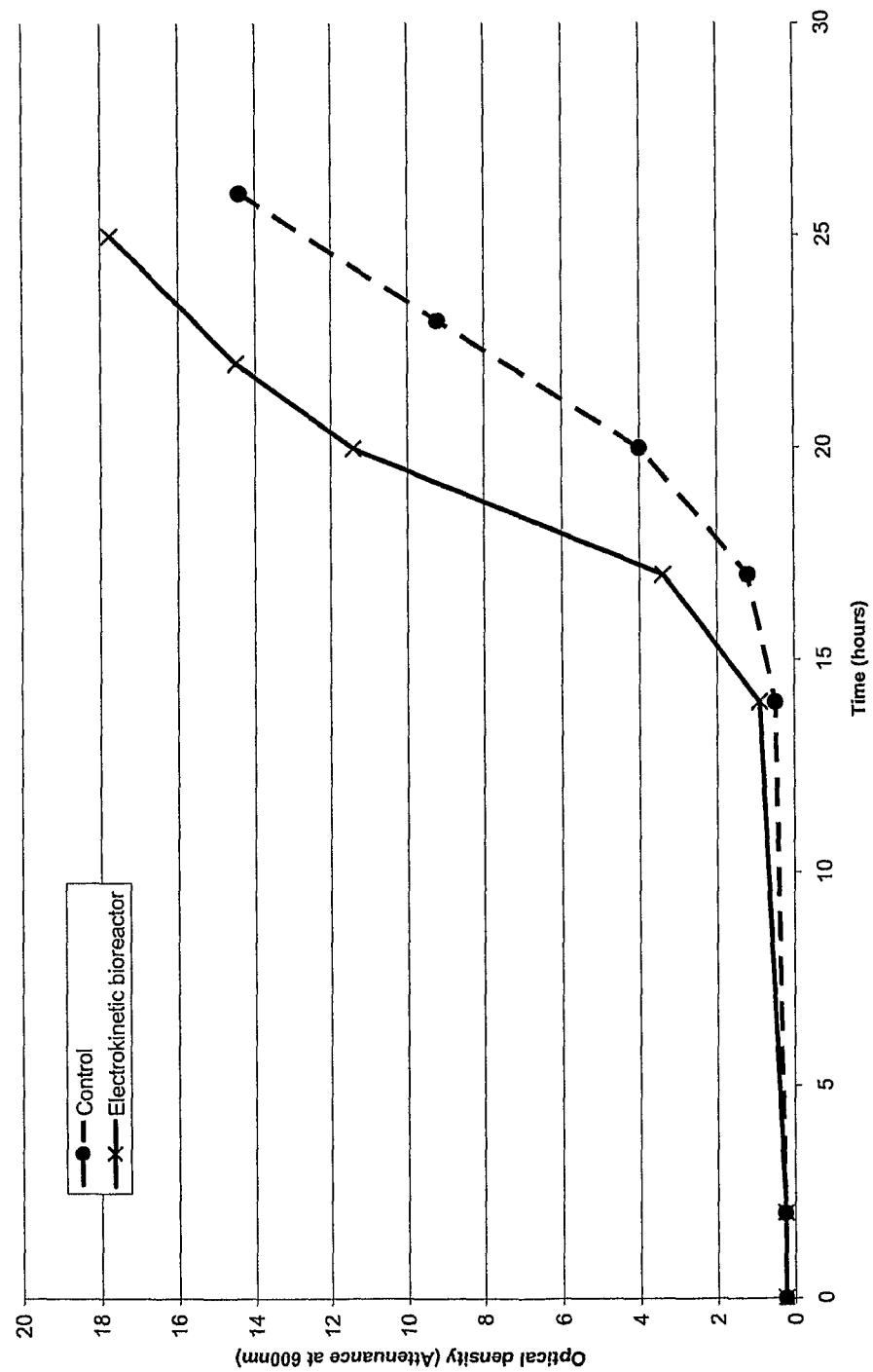
FIG. 1 shows the effect of the electokinetic bioreactor on the growth of *Clostridium acetobutylicum* (2 L fermentation, pH 6.6, 2×CGM, 150 rpm mixing). Dashed line shows the growth of the culture without the electrokinetic bioreactor; solid line shows the effect of the electrokinetic bioreactor on growth.

The results showed that the bacteria grown in the fermentor attached to the stack grew at a faster rate than those grown without the stack (FIG. 1).

The removal of acids from a fermentation vessel during the growth of a culture of a solventogenic micro-organism therefore leads to an increase in the growth rate of the organism.

Improved growth rate will lead to shorter fermentation times and therefore could improve productivity of solvent by solventogenic bacteria. The maximum optical density will be achieved faster than by conventional means. Acids removed from the vessel may be stored separately and added back to the fermentation when the maximum optical density has been achieved (or when the pH of the culture starts to rise).

Example 2

Figure 2:
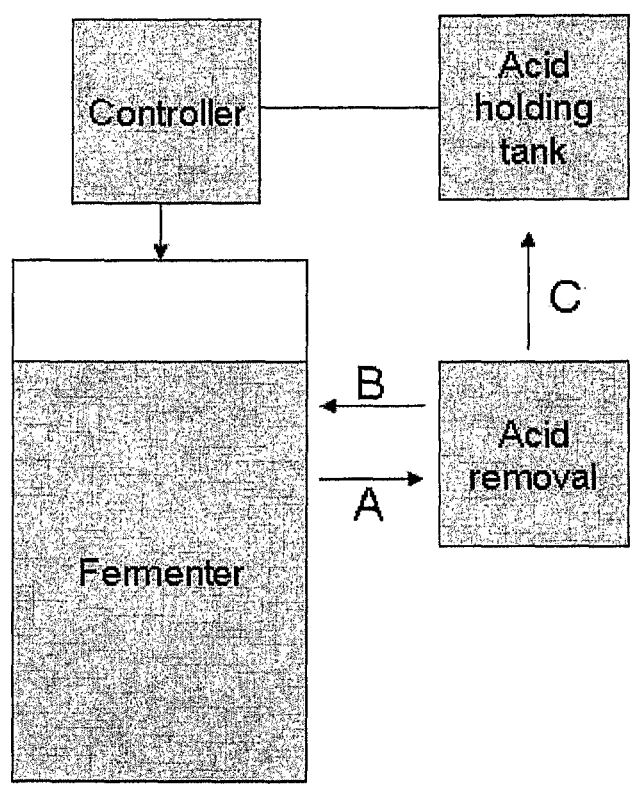
FIG. 2 shows a batch fermentation process where the micro-organisms are grown in a fermenter attached to an electrokinetic bioreactor. A=medium containing acid; B=acid depleted medium; C=acid.

A batch fermentation process where the micro-organisms are grown in an electrokinetic bioreactor (or in a fermenter attached to, an electrokinetic bioreactor). The reactor consistently strips the acid from the culture allowing improved growth. At the point at which the growth rate drops (transition phase), the acids are slowly reintroduced, and controlled at a rate that maintains a steady pH (a slow increase in pH is associated with solvent production). (See FIG. 2).

Example 3

Figure 3:
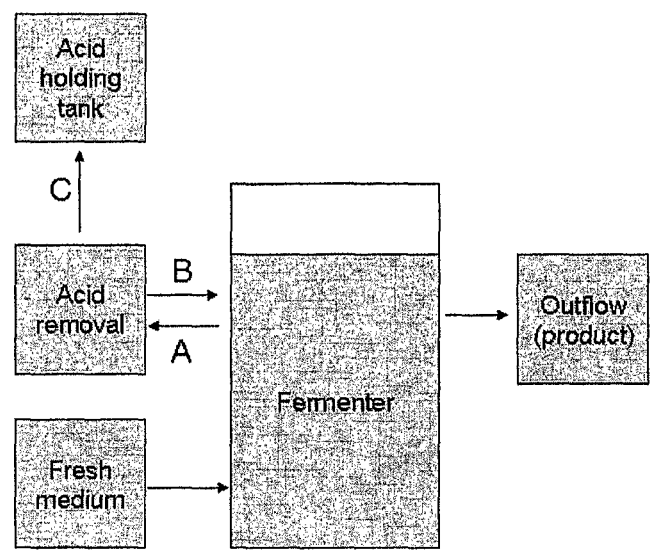
FIG. 3 shows a continuous fermentation process of the invention, where fresh media is introduced into the fermenter and a outflow containing the product (solvent) is harvested. A=medium containing acid; B=acid depleted medium; C=acid.

A batch fermentation process where the micro-organisms are grown in an electrokinetic bioreactor (or in a fermenter attached to an electrokinetic bioreactor). The reactor consistently strips the acid from the culture allowing improved growth (and therefore a longer exponential phase). At a point during exponential phase, the acids are slowly reintroduced in order to slow growth and induce the onset of solventogenesis (see FIG. 3).

Example 4a

Figure 4:
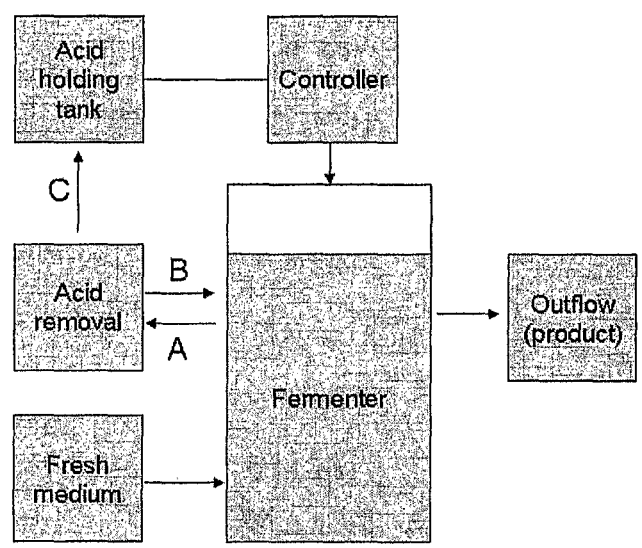
FIG. 4 shows a continuous fermentation process of the invention, where acid is reintroduced into the fermenter in a controlled manner. A=medium containing acid; B=acid depleted medium; C=acid.

A continuous fermentation process that is started in a fermenter without the application of an electrokinetic bioreactor, but when solventogenesis has started the process is maintained in a steady-state (acids and solvents are produced at the same time) and continued indefinitely. Acids are continuously stripped from the fermentation vessel in order to allow improved growth (see FIG. 4).

Example 4b

Alternatively, for strains that produce solvent during the early stages of growth, a continuous fermentation process may be used that is started in a fermenter attached to an electrokinetic bioreactor and maintained in a steady-state and continued indefinitely. Acids are continuously stripped from the fermentation vessel in order to allow improved growth (see FIG. 4).

Example 5

A continuous fermentation process that is started in a similar manner to Example 4b, so that acids are removed during the early growth phases. At a point during growth the acids are reintroduced to create and maintain the acidic conditions required for solvent production. The acids will also be converted to butanol (see FIG. 4).

Example 6

Figure 5:
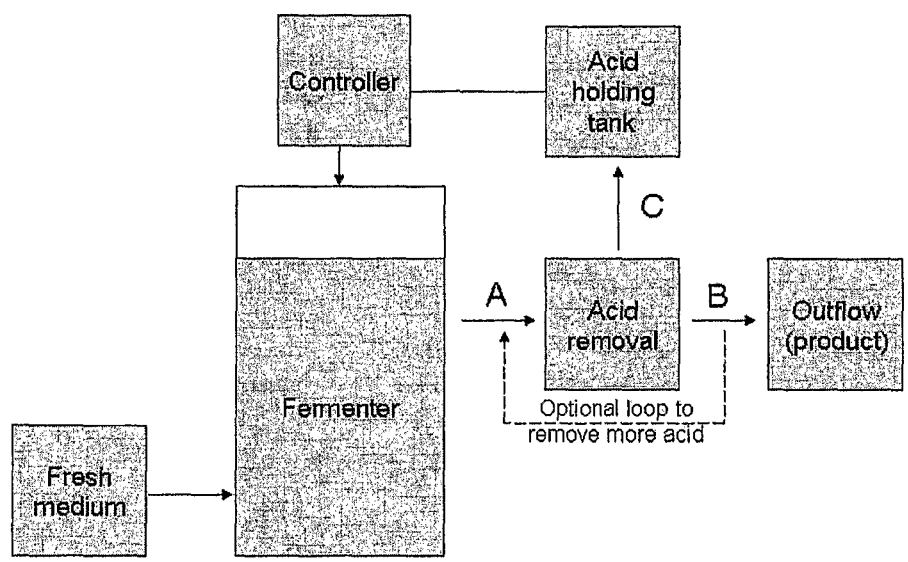
FIG. 5 shows a continuous fermentation process of the invention, where acid is removed in the outflow. A=medium containing acid; B=acid depleted medium; C=acid.

A continuous fermentation process similar to Example 5, but acid removal occurs in the outflow. Acids can then be fed back into the fermentation to lower the pH of the fermentation vessel to allow optimised solvent production (see FIG. 5).

Example 7

Figure 6:
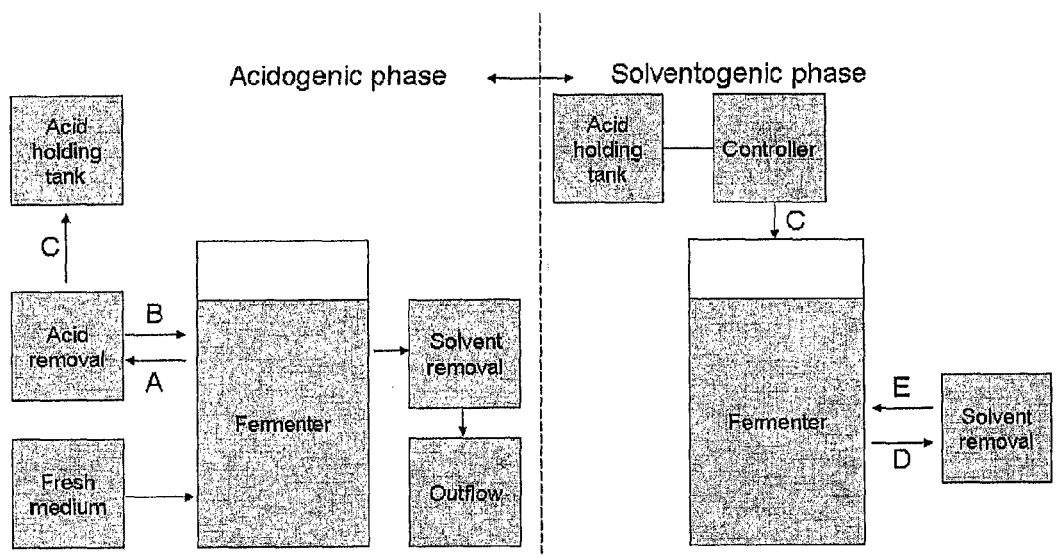
FIG. 6 shows a two stage continuous process of the invention. A=medium containing acid; B=acid depleted medium; C=acid; D=medium containing solvent; E=solvent-depleted medium.
Figure 7:
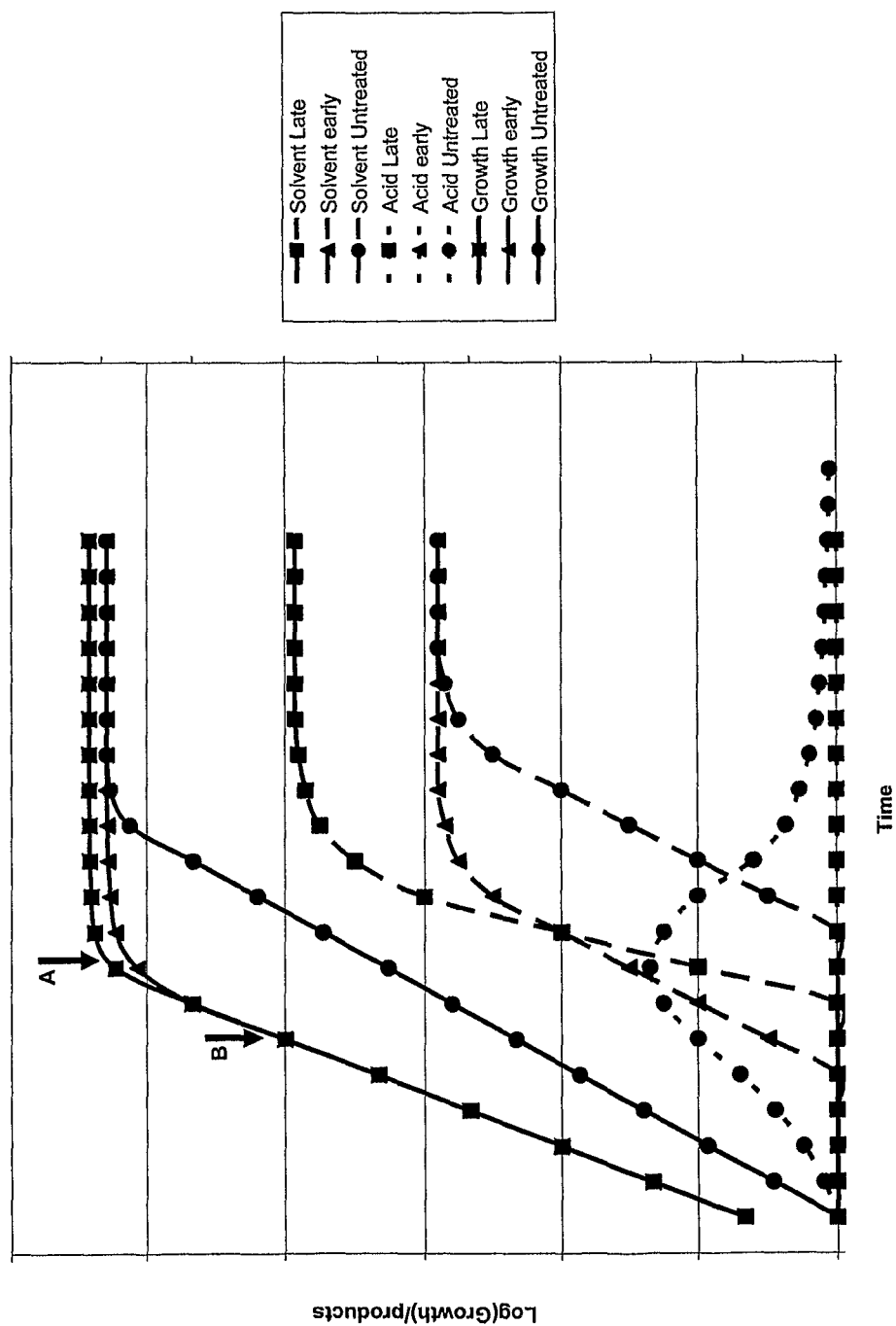
FIG. 7 shows growth curves of the effect of acid removal and reintroduction into the fermenter at different growth stages. Solid lines show growth, large dashed lines show solvent production, dotted line shows acid production (acid production is not seen in experiments where acid is removed). Lines plotted with squares show the effect of removing the acid throughout the exponential growth phrase and adding it back later (Arrow A—during transition or stationary phase). Triangles show the predicted effect of removing acid during the growth phase and adding it back during later during the exponential growth phase (Arrow B—before transition/stationary phase). Circles show the observed growth characteristics in a fermentation carried out without acid removal.

A two-phase continuous process that is started in a manner similar to Example 4b, but divided into acidogenic and solventogenic process phases (see FIG. 6).

During the acidogenic process phases, cells are allowed to grow at a maximal rate to establish a high rate of acid production and maximum conversion of sugars to acid; at this stage acids are stripped and stored in a separate vessel. Media containing a carbon source is fed into the fermentation vessel and outflow (containing reduced amounts of the carbon source, but increased amounts of acid) is passed through the electrokinetic bioreactor. Dilution rate of the vessel is adjusted to maximise growth and acid production.

At any given time the input of fresh medium containing the carbon source and the outflow are stopped (dilution rate=zero) to allow transition to a solventogenic process phase. During the solventogenic process phase, some of the acids are reintroduced to the fermenter for conversion to solvent, the solvent is removed by an undetermined method (e.g. gas-stripping, pervaporation, distillation), to allow maximal solvent production. It may also be necessary to add a low percentage of carbon source at this stage. Once the acids are reintroduced the pH will drop, but when solvent production starts the pH will begin to rise so the rate of addition of reintroduced acids is controlled by maintaining the low pH (preferably pH 4-5) of the vessel.

Solvent can be stripped from the fermenter vessel during the solventogenic phase in order to help prevent inhibition of growth or solvent could be allowed to accumulate in the solventogenic phase and removed from the outflow in the acidogenic phase as it is diluted by fresh media.

After complete conversion of the acid or at a point when conversion of acid to alcohol ceases (as indicated by a slow but consistent fall in pH), the fermentation vessel is returned to an acidogenic phase by restarting the carbon source feed and acid stripping (increase dilution rate). Cells will recover and grow exponentially after a lag phase.

Solvent extraction can be carried out either on the outflow during the acidogenic process phase or in the solventogenic process phase or during both process phases.

Repeated phases of acidogenesis and solventogenesis would constitute a continuous process.

Example 8

A batch or continuous fermentation where acids are stripped from a fermentation (that produces butanol) and used as a carbon source or intermediate for another non-solventogenic fermentation process (that can utilise butyrate/acetate as a carbon source). At the same time the bacteria in the fermentation vessel also produce solvents that can be removed by an undetermined process (e.g. gas-stripping, pervaporation, distillation).

What is claimed is:
1. A process for producing butanol, comprising:
(i) culturing a micro-organism in a culture medium in a culture vessel,
wherein the micro-organism is one which is capable of producing butyrate and butanol, wherein the micro-organism is a biphasic solvent-producing *Clostridia;*
(ii) transferring a first portion of butyric acid or acid derivatives thereof which are produced in the culture vessel to a separate compartment,
wherein the acid derivatives thereof are selected from the group consisting of metal salts of butyric acid, non-metal salts of butyric acid, butyric acid esters and butyramide;
(iii) introducing a second portion of the butyric acid or acid derivatives obtained from the separate compartment into the culture vessel; and
(iv) harvesting butanol from the culture vessel;
wherein the butyric acid or acid derivatives are reintroduced into the culture vessel at a rate which maintains a constant or substantially constant pH in the culture vessel, or wherein the butyric acid or acid derivatives are reintroduced into the culture vessel during an exponential growth phase in order to slow the growth of the micro-organism and/or to induce the onset of the solventogenic phase of the biphasic micro-organism,
wherein the culture vessel is the first compartment of an electrochemical reactor, wherein step (ii) comprises applying a direct current electric field across the electrochemical reactor with an anode and cathode, wherein the electrodes which are used to apply the electric field are separated from the culture medium such that any micro-organisms in the culture medium do not come into contact with said electrodes, wherein the electrochemical reactor further comprises a second compartment which is placed between the first compartment and the anode and is separated from the first compartment by an anion-selective membrane,
wherein anions in the first compartment are drawn through the anion-selective membrane by the electric field into the second compartment, from which they may be removed as acid or acid derivatives thereof; and
wherein step (iii) comprises introducing a second portion of the acid or acid derivatives obtained from the second compartment into the culture vessel.
2. A process for producing butanol, comprising:
(i) culturing a micro-organism in a culture medium in a culture vessel,
wherein the micro-organism is one which is capable of producing butyrate and butanol, wherein the micro-organism is a biphasic solvent-producing *Clostridia;*
(ii) transferring a first portion of butyric acid or acid derivatives thereof which are produced in the culture vessel to a separate compartment,
wherein the acid derivatives thereof are selected from the group consisting of metal salts of butyric acid, non-metal salts of butyric acid, butyric acid esters and butyramide;
(iii) introducing a second portion of the butyric acid or acid derivatives obtained from the separate compartment into the culture vessel; and
(iv) harvesting butanol from the culture vessel;
wherein the butyric acid or acid derivatives are reintroduced into the culture vessel at a rate which maintains a constant or substantially constant pH in the culture vessel, or wherein the butyric acid or acid derivatives are reintroduced into the culture vessel during an exponential growth phase in order to slow the growth of the micro-organism and/or to induce the onset of the solventogenic phase of the biphasic micro-organism,
wherein step (ii) comprises transferring at least a first portion of the culture medium from the culture vessel to the first compartment of an electrochemical reactor, and applying a direct current electric field across the electrochemical reactor with an anode and cathode,
wherein the electrochemical reactor further comprises a second compartment which is placed between the first compartment and the anode and is separated from the first compartment by an anion-selective membrane, wherein anions in the first compartment are drawn through the anion-selective membrane by the electric field into the second compartment, from which they may be removed as acid or acid derivatives thereof; and
wherein step (iii) comprises introducing a second portion of the acid or acid derivatives obtained from the second compartment into the culture vessel.
3. The process as claimed in claim 1,
wherein the butyric acid or acid derivatives are removed from the culture medium throughout, or substantially throughout, an exponential growth phase of the micro-organism.

4. The process as claimed in claim 1, wherein the butyric acid or acid derivatives obtained from the second compartment are stored in a reservoir prior to reintroduction into the culture vessel.

5. The process as claimed in claim 1, wherein a portion of the butyric acid or acid derivatives is reintroduced into the culture vessel at a late exponential phase, during a transition phase or during a stationary phase of the micro-organism's growth.

6. The process as claimed in claim 1, wherein the micro-organism is an anaerobic bacterium.

7. The process as claimed in claim 1, wherein the buffer in the culture vessel is a cationic buffer.

8. The process as claimed in claim 1, wherein a portion of the butyric acid or acid derivatives is reintroduced into the culture vessel during an early stationary phase of the micro-organism's growth.

9. The process as claimed in claim 1, wherein the micro-organism is *Clostridium acetobutylicum*.

10. The process as claimed in claim 2, wherein the butyric acid or acid derivatives are removed from the culture medium throughout, or substantially throughout, an exponential growth phase of the micro-organism.

11. The process as claimed in claim 2, wherein the butyric acid or acid derivatives obtained from the second compartment are stored in a reservoir prior to reintroduction into the culture vessel.

12. The process as claimed in claim 2, wherein a portion of the butyric acid or acid derivatives is reintroduced into the culture vessel at a late exponential phase, during a transition phase or during a stationary phase of the micro-organism's growth.

13. The process as claimed in claim 2, wherein the micro-organism is an anaerobic bacterium.

14. The process as claimed in claim 2, wherein the buffer in the culture vessel is a cationic buffer.

15. The process as claimed in claim 2, wherein a portion of the butyric acid or acid derivatives is reintroduced into the culture vessel during an early stationary phase of the micro-organism's growth.

16. The process as claimed in claim 2, wherein the micro-organism is *Clostridium acetobutylicum*.

\* \* \* \* \*